United States Patent [19]

Choisser

[11] Patent Number: 4,842,516
[45] Date of Patent: Jun. 27, 1989

[54] DISPOSABLE HAND TOOL FOR HEALTH CARE PROCEDURES

[76] Inventor: George P. Choisser, 14130 Michael St., Orland Park, Ill. 60462

[21] Appl. No.: 154,397

[22] Filed: Feb. 10, 1988

[51] Int. Cl.$^4$ .................................................. A61C 1/05
[52] U.S. Cl. ...................................... 433/132; 433/166; 433/125
[58] Field of Search ................ 433/132, 101, 125, 166

[56] References Cited

U.S. PATENT DOCUMENTS

| Re. 24,391 | 11/1957 | McFadden | 433/132 |
| 2,937,444 | 5/1960 | Kern | 433/132 |
| 3,192,922 | 7/1965 | Winkler | 433/132 |
| 3,855,704 | 12/1974 | Booth | 433/101 |
| 3,955,284 | 5/1976 | Balson | 433/132 |

Primary Examiner—John J. Wilson
Attorney, Agent, or Firm—Ernest Kettelson

[57] ABSTRACT

A disposable hand tool for performing dental and other health care procedures in which the entire tool is thrown away and disposed of after use with a single patient. The tool is made of relatively inexpensive materials such as plastic, and since durability and re-use are not requirements the operating mechanism can itself be constructed of disposable materials, including non-metallic materials. In the embodiment described herein, the disposable hand tool has a rotatable working member such as a rotatable buffer for polishing and cleaning teeth known in the dental profession as a prophylactic angle or cup, a rotatable burr also for use by dentists, and the like. The rotatable operating mechanism includes a small turbine of plastic or other disposable material mounted for rotation in a hand held housing which is also made entirely of disposable material and connectable to a hose which in turn is connected to a source of compressed air to drive the turbine. The rotatable prophylactic cup, rotatable burr, or other working member may be integrally and non-removably connected to the drive shaft of the turbine, since the working member itself is thrown away with the disposable hand tool after use with a single patient.

9 Claims, 3 Drawing Sheets

DISPOSABLE HAND TOOL FOR HEALTH CARE PROCEDURES

BACKGROUND OF THE INVENTION

This invention relates to the field of hand tools for dentists and others in the health care profession which are used to perform dental and other health care procedures, such as those used to polish, clean and brush teeth. In particular, this invention relates to those which are disposable after a single use.

People who work in the health care fields such as dentists, doctors, nurses, technicians and the like have become increasingly concerned about the growing risks to their patients as well as to themselves from treating someone who may have a communicable disease and which may be transmitted to others. To minimize the risk, various proposals have been made to use protective coverings to reduce the possibility of contaminated blood, viruses, bacteria and other transmission agents from reaching the doctor's or dentist's hands, as well as from reaching instruments and tools he may be using so they can be used again. The protective coverings such as gloves, shields and the like are made of disposable materials and thrown away after a single use. However, the tool itself, such as a dentist's hand piece or air syringe which have been made for re-use, relatively long duration, and are accordingly expensive, have not been heretofore thrown away after a single use. Even if they are protected by some sort of a protective covering which is itself thrown aray, the possibility still exists that the tool has become contaminated since parts are necessary in direct contact with patients. If the tools are to be re-used on other patients, they have to be cleaned and sterilized which means that the dentist, doctor or an assistant may very easily suffer a scratch while performing the cleaning operation by which disease carrying blood, viruses, bacteria and the like on the tool could enter the blood stream of the one handling the tool.

The present invention solves this problem and maximizes protection against transmission of disease by disposing of the entire tool after use on a single patient, and by making such tools of materials which are inexpensive enough to make such disposal feasible and by providing operating structures which are durable enough for use with single patient but less expensive than those needed for long operating life and a large number of re-uses.

SUMMARY OF THE INVENTION

It is an object of the invention to provide a disposable hand tool for performing a variety of dental and other health care procedures which may be thrown out and disposed of in its entirety after use with a single patient.

It is an object of the invention to provide a disposable hand tool for performing dental and other health care procedures which is made of inexpensive disposable materials, having a less expensive operating mechanism than those intended for multiple re-use, and having the working member of such tool which is normally removable made integrally connected to and non-removable from the disposable hand tool itself.

It is an object of the invention to provide a disposable hand tool for performing dental and other health care procedures having operating parts and connectable to a source of compressed air to drive such operating parts which may be disconnected from such source of compressed air and disposed of in its entirety after use with a single patient, such hand tool having connecting means which enables easy disconnection of the used one after use with one patient and easy connection of a new one for use with the next patient.

It is an object of the invention to provide a disposable hand tool for performing dental and other health care procedures which is disposable in its entirety after use with a single patient and which does not require any post-operative or post-procedure handling other than placing in a disposal receptacle for disposal.

DESCRIPTION OF PREFERRED EMBODIMENT

Figure 1:
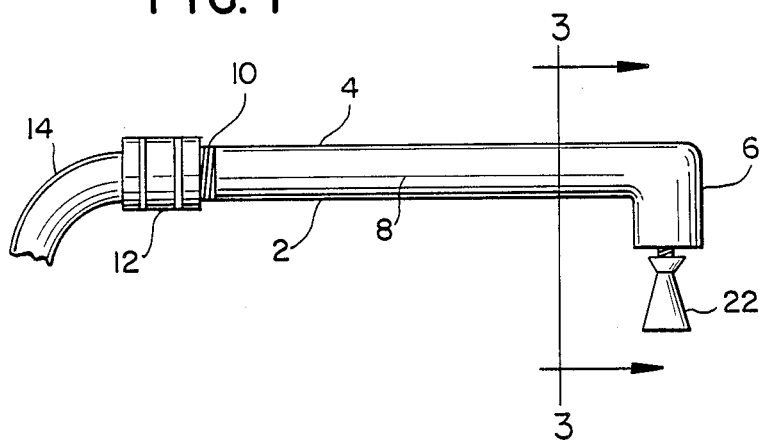
FIG. 1 is a side elevation view of a disposable hand tool for performing various dental operations in accordance with this invention.
Figure 2:
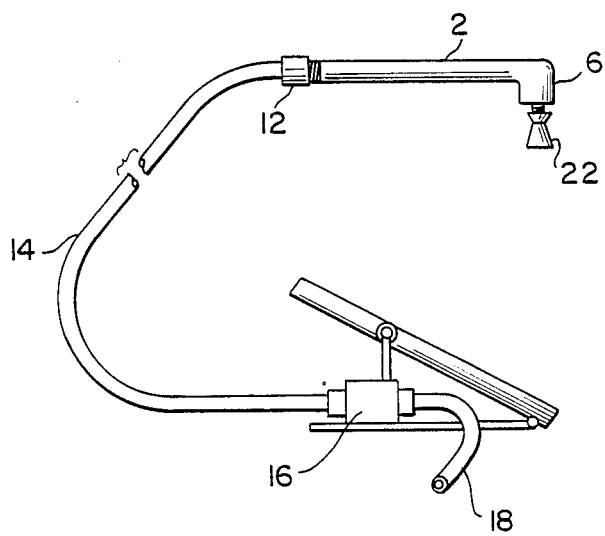
FIG. 2 is a side elevation view of a disposable hand tool as shown in FIG. 1, showing its connection to a foot operated pedal valve which in turn is connected to a source of pressurized air, the air hose being segmented and the pressurized air source not being shown.
Figure 3:
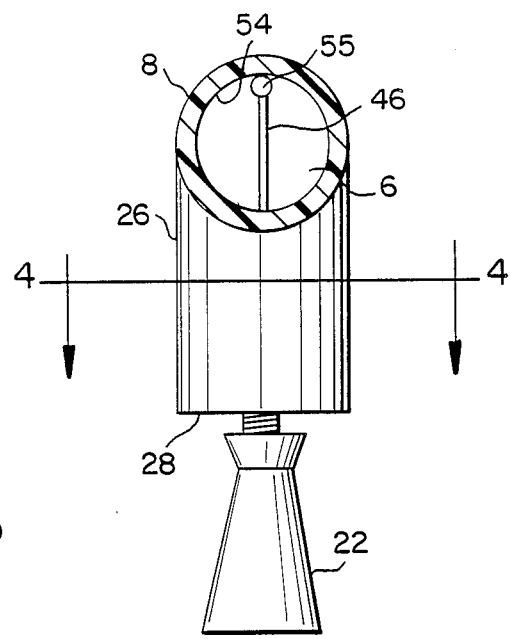
FIG. 3 is a section view taken on line 3—3 of FIG. 1 showing the air passageway of the hand tool and its entrance to the operating chamber.
Figure 4:
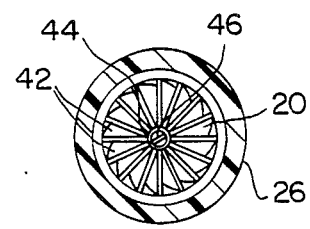
FIG. 4 is a section view taken on line 4—4 of FIG. 3 showing the operating chamber and turbine seated therein.
Figure 5:
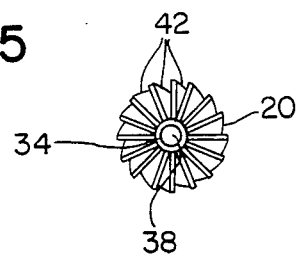
FIG. 5 is a bottom plan view of the turbine used in the disposable hand tool in accordance with this invention.
Figure 6:
FIG. 6 is a plan view of the friction reducing ring between the bottom of the turbine and the end wall of the operating chamber as shown in FIG. 7.
Figure 7:
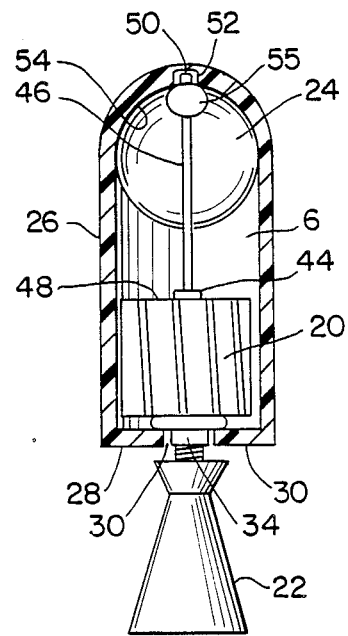
FIG. 7 is an end elevation view of the operating mechanism of the hand tool with the end wall of the operating chamber being cut away and shown in section.

A disposable rotary tool assembly for use in dental procedures in accordance with this invention includes a relatively rigid disposable hand tool 2 made of a relatively inexpensive plastic material, having an elongated tubular portion or barrel 4 terminating at one end in an L-bend operating chamber 6. The cylindrical wall 8 of the barrel 4 is provided with external threads 10 at the opposite end for connection to a threaded coupling 12 of an air hose 14 leading to a foot operated pedal valve 16, which is connected by air hose 18 to a pressurized air supply.

The pedal valve 16 is located on the floor at the side of the dentist's work chair, and is normally biassed to the valve closed position. Pressurized air is fed to the disposable hand tool 2 when connected to the air hose 14 by the dentist pressing down on the pedal valve 16 which opens the valve and admits pressurized air for operation of a turbine 20 mounted for rotation in the operating chamber 6 of the disposable hand tool 2.

The air hose 14 leading from the pedal valve 16 to the disposable hand tool 2 is long enough to enable the dentist to use the particular cleaning, brushing, polishing, grinding or other dental tool connected thereon for working on the teeth of a patient in the dental chair.

The particular dental tool shown in the drawings is known as a prophylactic angle, or prophylactic cup 22. Other rotatable dental tools may be connected to and used with the disposable hand tool 2 in accordance with this invention, such as a dental burr, a rotating brush, and the like. Whatever dental tool is connected to the disposable hand tool 2 in accordance with this invention is permanently connected as an integral part of the unit and is disposed of with the hand tool 2 itself after use with a single patient.

The cylindrical wall 8 of the barrel 4 surrounds an elongated air passageway 24 which opens at one end for connection to the air hose 14 and at the opposite end to the operating chamber 6. The operating chamber 6 includes a cylindrical wall 26 extending in a direction normal to that of the barrel 4. It terminates at a free end 28 having an end wall 30 across the free end 28 of the operating chamber 6. A circular aperture 32 extends through the end wall 30 at its center to receive for rotation the integrally formed cylindrical axle 34 of the turbine 20 which extends from its bottom side 36. The axle 34 seated in aperture 32 of the end wall 30 serves to hold turbine 20 in axial alignment with the central axis of the operating chamber 6 while it rotates in response to the flow of pressurized air. The external diameter of the axle 34 is slightly smaller than the internal diameter of the circular aperture 32 to permit free rotation of the axle 34 therein.

The axle 34 includes a threaded bore 38 to receive and hold the threaded shank 40 of the prophylactic cup 22 or other dental tool.

The turbine 20 includes angled vanes 42 extending outwardly from its central hub 44. An elongated stabilizing shaft 46 is connected to the central hub 44 on the top side 48 of the turbine 20, the free end 50 of the elongated stablizing shaft 46 seating in a cylindrical recess 52 formed in the roof portion 54 of the operating chamber. The elongated shaft 46 serves to stabilize the turbine 20 during rotation and to keep it in axial alignment with the central axis of the operating chamber 6 while rotating. A spherical bearing member 55 is formed or affixed to the shaft 46 near its upper free end but spaced apart inwardly thereof equal to that end portion of shaft 46 which seats in the cylindrical recess 52. The spherical bearing member 55 bears against the roof portion 54 to restrain the turbine 20 from axial movement in the direction to the roof portion 54.

This axle bearing structure for the turbine, of an integrally formed axle 34 on one side received for rotation in circular aperture 32 of end wall 30 of the operating chamber and the elongated shaft 46 extending from the other side received for rotation in the cylindrical recess 52 in the roof 54 of the operating chamber, provides an economical means for operationally mounting the turbine. Since the entire unit is to be thrown out and disposed of after use with a single patient, a more durable and expensive axle and bearing structure is not needed.

To reduce friction of the bottom surface 36 of the turbine 20 if it were to rotate in direct contact with the end wall 30, a reduced diameter ring bearing 56 is provided having an outer diameter less than that of the turbine 20 and a central aperture having an inner diameter greater than the external diameter of the turbine axle 34. The axle 34 extends through the ring bearing 56 and into the circular aperture 32 of the end wall 30 when the turbine 20 is seated in place in the operating chamber 6.

The turbine may be made of a rigid plastic material such as vinyl, or hard rubber.

All parts of the disposable rotary tool assembly in accordance with this invention may be of non-metallic materials.

An essential purpose of the invention is disposal of the entire unit after use with a single patient to minimize the potential risk of transmitting disease from one patient to another, as well as from patient to doctor and his assistants which can occur if tools are cleaned and otherwise handled by them for later re-use.

Operation of this invention is as follows. Dental offices are equipped with air compressors or other sources of pressurized air to operate air syringes and the like usee in various dental procedures. Air hoses from such sources of compressed air lead to the dental chair and a pedal valve on the floor next to the dental chair which the dentist can operate with his foot leaving his hands free to work on the patient. Typically a dentist will have both a high speed and a low speed compressed air line at the side of his dental chair, to which his various re-useable dental tools are connected for operation.

The disposable hand tool 2 in accordance with the present invention can take the place of the re-useable dental tools presently being used for many of the existing dental procedures. The particular dental tool desired is already in place, non-removably connected to the disposable hand tool 2. Instead of connecting an expensive dental hand piece or air syringe to the compressed air line, one of the disposable hand tools 2 in accordance with this invention having the working tool desired connected thereto is connected to the air hose 14 at the dental chair. The barrel 4 is of a convenient length for the dentist to hold in his hand. The operating chamber 6 is small enough for convenient use in and about the patients mouth. When the prophylactic cup 22, or whatever other tool is connected, is in position for use on the patient, the dentist depresses the pedal valve 16 which admits compressed air through the air line 14, through the passageway 24 of the hand tool 2 and into the operating chamber 6. The compressed air in the operating chamber causes the turbine 20 to rotate, and with it the integrally formed axle 34 seated in the end wall aperture 32 one side and the elongated stabilizing shaft 46 seated in the cylindrical roof recess 52 on the other, which keep the turbine 20 and its central hub 44 in axial alignment with the central axis of the operating chamber 6.

The prophylactic cup 22 connected by threaded shank 40 to the rotating turbine axle 34 is thereby rotated for use on the patient.

Rotation of the prophylactic cup or other tool is stopped by the dentist releasing the pedal valve 16 which is normally biased to the valve closed position.

As soon as the dental procedure has been completed for the patient on which it was used, the disposable hand tool 2 is disconnected from the air line 14 and the entire unit is placed in a disposal bag or other appropriate receptacle for disposal. If the dentist is wearing sanitary gloves, disconnection and disposal is preferably done while the gloves are still on to maximize protection against transmission of infectious disease.

The disposable hand tool in accordance with this invention is useable by anyone who performs health care procedures which requires the use of a tool operated by compressed air. Its features of maximizing protection against transmissions of disease is available to all health care practioners and is not limited to the dental profession.

The dental tool or other health care tool connected to the turbine 20 for rotation therewith may be integrally connected thereto, so it cannot be removed for replacement and re-use, such as by welding or gluing the shank 40 of prophylactic up 22 in the bore 38 of axle 34. These parts may all be of plastic and may be permanently secured to each other by heat welding and other known forms of permanent bonding.

I claim:

1. A disposable hand tool for performing dental and other health care procedures on a single patient and a repeatedly useable flexible power supply hose combination, said disposable hand tool comprising a disposable structure to be disposed of after use with a single patient to support a turbine therein for rotation, connecting means for connection of said disposable structure to said repeatedly useable flexible power supply hose, said disposable structure having an operating chamber section to receive and rotatably support said turbine therein for use in close proximity to a said patient, an elongated section integrally joined to said operating chamber section to provide a hand grasp means for manipulating said operating chamber section and said turbine when in use on a said patient and to space said operating chamber section when used in close proximity to a said patient apart from said flexible power supply hose to keep it out of close proximity to a said patient, a passageway in said disposable structure to direct a supply of pressurized fluid to said turbine to cause it to rotate, a tubular wall portion of said disposable structure surrounding said passageway and a tool for performing a dental or health care procedure connected to said turbine for rotation therewith, wherein said operating chamber section is bounded by a tubular side wall, said tubular side wall of said operating chamber being integrally formed with and extending from said elongated tubular wall portion surrounding said passageway at an oblique angle thereto.

2. A disposable hand tool for performing dental and other health care procedures on a single patient and a repeatedly useable flexible power supply hose combination as set forth in claim 1, wherein said operating chamber section is smaller in its peripheral dimensions than a human's mouth and is insertable therein for performing said dental or health care procedure in and about a said human's mouth.

3. A disposable hand tool for performing dental and other health care procedures on a single patient and a repeatedly useable flexible power supply hose combination as set forth in claim 1, wherein said tool for performing a dental or health care procedure is a prophylactic cup, said prophylactic cup being integrally and non-removably connected to said turbine for rotation therewith.

4. A disposable hand tool for performing dental and other health care procedures on a single patient and a repeatedly useable flexible power supply hose combination, said disposable hand tool comprising a disposable structure to be disposed of after use with a single patient to support a turbine therein for rotation, connecting means for connection of said disposable structure to said repeatedly useable flexible power supply hose, said disposable structure having an operating chamber section to receive and rotatably support said turbine therein for use in close proximity to a said patient, an elongated section integrally joined to said operating chamber section to provide a hand grasp means for manipulating said operating chamber section and said turbine when in use on a said patient and to space said operating chamber section when used in close proximity to a said patient apart from said flexible power supply hose to keep it out of close proximity to a said patient, a passageway in said disposable structure to direct a supply of pressurized fluid to said turbine to cause it to rotate, a tubular wall portion of said disposable structure surrounding said passageway and a tool for performing a dental or health care procedure connected to said turbine for rotation therewith, wherein said operting chamber section includes a turbine chamber portion having a cylindrical side wall and an end wall, a circular aperture through said end wall, said turbine being rotatably seated in said turbine chamber portion, said turbine having a central hub and a plurality of vanes extending radially outwardly from the hub, said hub and said turbine having a first end facing in one direction and an opposite second end facing the opposite direction, said first end of said hub and said turbine including a first cylindrical shaft projecting axially therefrom, said first cylindrical shaft being received for rotation in said circular aperture through said end wall of said turbine chamber portion of said operating chamber.

5. A disposable hand tool for performing dental and other health care procedures on a single patient and a repeatedly useable flexible power supply hose combination as set forth in claim 4, including a second cylindrical shaft projecting axially from said second end of said hub and turbine, bearing means in said operating chamber section to support said second cylindrical shaft, said first and second cylindrical shafts thereby maintaining said turbine axially aligned with the central axis of said turbine chamber portion of said operating chamber section while being rotated.

6. A disposable hand tool for performing dental and other health care procedures on a single patient and a repeatedly useable flexible power supply hose combination as set forth in claim 5, wherein said operating chamber section includes a roof portion spaced apart from and facing said second end of said hub and turbine, said bearing means in said operating chamber section to support said second cylindrical shaft includes a recess in said roof portion opening to face said second end of said hub and turbine and to receive the free end of said second cylindrical shaft therein, including said free end of said second cylindrical shaft.

7. A disposable hand tool for performing dental and other health care procedures on a single patient and a repeatedly useable flexible power supply hose combination as set forth in claim 6, wherein said second cylindrical shaft includes a radially projecting annular portion spaced apart inwardly from said free end thereof to bear against said roof portion when said free end of said second cylindrical shaft is received in said recess in said roof portion.

8. A disposable hand tool for performing dental and other health care procedures on a single patient and a repeatedly useable flexible power supply hose combination as set forth in claim 4, wherein said first cylindrical shaft is integrally formed with said turbine and rotates therewith.

9. A disposable hand tool for performing dental and other health care procedures on a single patient and a repeatedly useable flexible power supply hose combination as set forth in claim 8, wherein said integrally formed first cylindrical shaft of said turbine includes a central bore therein, said tool for performing a dental or health care procedure including a connecting stem extending from an end thereof, said stem being receivable in said central bore of said integrally formed first cylindrical shaft of said turbine to connect said tool in said turbine for rotation therewith.

* * * * *